United States Patent [19]

Moser et al.

[11] 4,110,451

[45] Aug. 29, 1978

[54] ANTIINFLAMMATORY IMIDAZOTHIAZOLES AND THIAZOLOPYRIMIDINES

[75] Inventors: Robert E. Moser, Mentor; Larry J. Powers, Madison; Zaven S. Ariyan, Mentor, all of Ohio

[73] Assignee: Diamond Shamrock Corporation, Cleveland, Ohio

[21] Appl. No.: 755,276

[22] Filed: Dec. 29, 1976

Related U.S. Application Data

[62] Division of Ser. No. 650,318, Jan. 19, 1976, Pat. No. 4,041,167.

[51] Int. Cl.$^2$ .................. A61K 31/425; A61K 31/505
[52] U.S. Cl. ...................................... 424/251; 424/270
[58] Field of Search ................... 424/251; 260/251 A

[56] References Cited

U.S. PATENT DOCUMENTS

| | | | |
|---|---|---|---|
| 3,594,378 | 7/1971 | Laliberte et al. | 260/251 A |
| 3,671,526 | 6/1972 | Manning | 260/251 A |
| 3,686,173 | 8/1972 | Houlihan et al. | 260/251 A |
| 3,740,394 | 7/1973 | Baily | 260/251 A |
| 3,860,718 | 1/1975 | Kuhla | 424/270 |

OTHER PUBLICATIONS

Canadian Journal of Chem., vol. 47-, 2843-2847 (1969).

*Primary Examiner*—Stanley J. Friedman
*Attorney, Agent, or Firm*—Stuart L. Melton

[57] ABSTRACT

Certain imidazothiazoles and thiazolopyrimidines have been found to prevent and inhibit the formation of granuloma tissue in animals. This result is accomplished by administering to the animal subject a therapeutically effective amount of a compound having the formula:

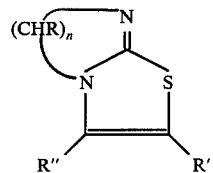

wherein R is hydrogen or methyl, R' is hydrogen, lower alkyl or thioalkyl, carboxy methyl, or phenyl; R" is lower alkyl, 2-benzofuranyl, naphthyl, phenyl, or mono- or disubstituted phenyl. The hydrated precursors of certain of these compounds as well as the acid addition and quaternary salts of both the compounds and their hydrated precursors may be employed.

7 Claims, No Drawings

ANTIINFLAMMATORY IMIDAZOTHIAZOLES AND THIAZOLOPYRIMIDINES

This is a division, of application Ser. No. 650,318, filed Jan. 19, 1976 now U.S. Pat. No. 4,141,167.

BACKGROUND OF THE INVENTION

Many compounds are known which exhibit some degree of antiinflammatory activity.

For example, British Pat. No. 1,099,389 discloses certain 2,4-disubstituted thiazoles which are known to be antiinflammatory. However, these compounds suffer from certain inherent deficiencies which limit their utility as antiinflammatory drugs. Also, in U.S. Pat. No. 3,796,800 is disclosed another group of thiazoles which exhibit antiinflammatory properties. These compounds are generally identified by the formula:

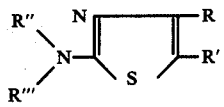

wherein R is lower alkyl (e.g., —CH$_3$), or N-aminocarbamoyl; R" and R"' are independently selected from the group consisting of hydrogen, lower alkyl (e.g., —C$_2$H$_5$) and lower acyl (e.g., —COCH$_3$); and R' is hydrogen, CONHR$_1$ or CONR$_2$R$_3$, is phenyl, mono-, di- or tri-(lower) alkylphenyl, cyclohexyl, or amino; R$_2$ is lower alkyl (C$_1$–C$_3$); R$_3$ is lower alkyl (C$_2$–C$_3$) or phenyl; or R$_2$ and R$_3$ together with the nitrogen atom form a morpholino ring, and pharmaceutically acceptable acid addition salts thereof, such as the hydrochloride.

While the above compounds evidence antiinflammatory properties, they also exhibit certain properties which limit their utility as such drugs.

From the Canadian Journal of Chemistry (Vol. 47, pg. 2847, 1969) certain [2,1-b] thiazoles and thiazolo [3,2-a] pyrimidines are known as anthelmintics. 3-(Hydroxy- or methoxy)-phenyl-5,6-dihydroimidazo-[2,1-b] thiazoles are known from U.S. Pat. No. 2,969,369 to have a variety of pharmaceutical activities, including an antiinflammatory effect. Further, U.S. Pat. No. 3,860,718 describes the use of quaternary 7-substituted imidazo [2,1-b] thiazolium compounds as hypoglycemic agents (blood-sugar lowering agents), but no disclosure can be found therein which would indicate that such compounds have antiinflammatory properties.

STATEMENT OF THE INVENTION

Therefore, it is an object of the present invention to provide effective antiinflammatory compositions containing as the active ingredients thereof certain imidazothiazoles and thiazolopyrimidines.

It is a further object of the present invention to provide a method for preventing and inhibiting the formation of granuloma tissue in animals employing certain imidazothiazoles and thiazolopyrimidines.

It is a still further object of the present invention to provide an imidazothiazole and certain hydrated precursors of imidazothiazoles and thiazolopyrimidines which have pharmaceutical activity.

These and further objects of the present invention will become apparent to those skilled in the art from the specification and claims which follow.

There has now been found a pharmaceutical preparation in dosage unit form, the active ingredient of which consists of a nontoxic antiinflammatory amount of at least one compound of the formula:

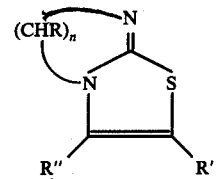

wherein n is 2 or 3; R is hydrogen or methyl; R' is hydrogen, C$_1$–C$_3$ alkyl or thioalkyl, phenyl, or carboxy methyl; and R" is C$_1$–C$_4$ alkyl, 2-benzofuranyl, naphthyl, phenyl, or mono- or di-substituted phenyl, and acid addition and quaternary salts thereof.

A method of preventing and inhibiting the formation of granuloma tissue in an animal subject has further been found, which method comprises administering to said animal a nontoxic antiinflammatory amount of at least one such compound.

There have further been found 3-(2-benzofuranyl)-5,6-dihydro-4H-imidazo-[2,1-b] thiazole and certain hydrated precursors of imidazothiazoles and thiazolopyrimidines having the formula:

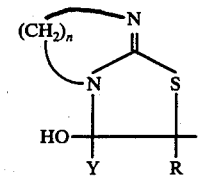

wherein n is 2 or 3; R is H or CH$_3$; and Y is phenyl or p-chloro-or p-methoxyphenyl. These compounds also have antiinflammatory effect and may be employed in the acid addition or quaternary salt form.

DESCRIPTION OF THE PREFERRED EMBODIMENTS

Compounds which are the active ingredients of the present invention fit the general formula:

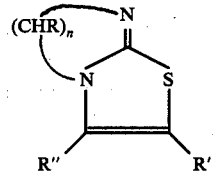

In this formula, when n is 2, the compounds are designated generally as substituted 5,6-dihydro-4H-dihydro-4H-imidazo-[2,1-b] thiazoles. When n is 3, the compounds are designated as substituted tetrahydro-thiazolo-[3,2-a] pyrimidines. The substituent R, of which 1 may be present on each methylene group, represents either hydrogen or methyl. The groups represented by R' include hydrogen, C$_1$–C$_3$ alkyl (especially methyl and ethyl) and thioalkyl (especially thiomethyl), carboxy methyl; and phenyl. The members fitting the definition for R" include C$_1$–C$_4$ alkyl (especially methyl and tertiarybutyl), 2-benzofuranyl, naphthyl, phenyl, and mono- or disubstituted phenyl (especially wherein the substituents are electronegative and in the "para"

position, such as Cl, Br, NO₂, OCH₃, and 3,4-dichloro- or dimethyl). A preferred and novel compound at this time is 3-(2-benzofuranyl)-5,6-dihydro-4H-imidazo[2,1-b] thiazole (including salts thereof). Preferred and novel hydrated precursors of the above formula are those corresponding to the formula:

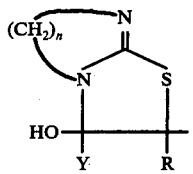

wherein n is 2 or 3; R is H or methyl; and Y is phenyl or p-chloro- or p-methoxyphenyl.

While the compounds themselves exhibit excellent antiinflammatory activity, they may be and often are employed in the form of pharmacologically acceptable acid addition or quaternary salts thereof. For example, one may employ acid halides, such as HBr or HCl, or tartaric acid, to form the addition salts or alkyl halides and the like, such as propargyl bromide, for quaternization. The criteria for choosing and methods for preparing salts suitable for administration are well known to those skilled in the art.

In preparing the pharmaceutical compositions of the present invention in unit dosage form, a nontoxic, antiinflammatory amount of one or more of the compounds of the present invention is incorporated with the appropriate carriers and/or diluents. Generally, the amount for administration will be from about 10 to 500 milligrams/kilogram/day of body weight, preferably from about 50 to 300 mg/kg/day.

For example, in the case of a tablet, the composition will comprise, in addition to the active ingredient, fillers, binders, and diluents such as lactose, methylcellulose, talc, gum tragacanth, gum acacia, agar, polyvinylpyrrolidone, stearic acid, and/or corn starch, etc. In the case of a liquid suspension for oral administration, the composition will comprise, in addition to the active ingredients, a filler such as sodium carboxymethylcellulose and/or syrup, e.g., a glycerine based syrup. In the case of a parenteral solution or suspension, the composition will comprise, in addition to the active ingredient, a suitable solvent or other liquid such as a saline solution. In the case of a topical ointment, a vehicle such as petroleum jelly or hydrophillic petroleum is suitable.

The compounds employed in the instant invention may be prepared by the condensation of an α-haloketone with (1) 2-mercaptoimidazoline or a substituted derivative to yield the desired (substituted) 5,6-dihydro-4H-imidazo-[2,1-b] thiazole or (2) with 1,2,3,4-tetrahydro-2-pyrimidinethiol or a substituted derivative to yield the desired (substituted) tetrahydrothiazolo-[3,2-a] pyrimidine. Reference to such standard preparations is set forth in the Canadian Journal of Chemistry, Vol. 47 (1969) at page 2843. Examples of the preparation of certain compounds of the instant invention follow.

EXAMPLE 1

To a refluxing solution of 3-benzoyl propionic acid (18 gm) in CHCl₃ (100 ml) was added bromine (16.2 gm) in CHCl₃ (100 ml). After 10 minutes of refluxing, the reaction mixture was cooled and the CHCl₃ removed in vacuo. 2-Imidazolidine (10.2 gm) in absolute ethanol was added and the reaction mixture heated to reflux for 1 hour. The reaction mixture was cooled and the precipitate separated by filtration. The product was recrystalized from 95% ethanol. The isolated product (5.5 gm) has a melting point of 258°–263° C. and was found to be 3-phenyl-5,6-dihydro-4H-imidazo[2,1-b] thiazo-2-ylacetic acid hydrobromide.

EXAMPLE 2

Similarly, for the preparation of 2-methylthio-3-t-butyl-5,6-dihydro-4H-imidazo-[2,1-b] thiazole hydrobromide, the procedure of Example 1 was followed except 1-methylthiopinacolone (10.7 gm) was brominated (11.4 gm) for the desired intermediate.

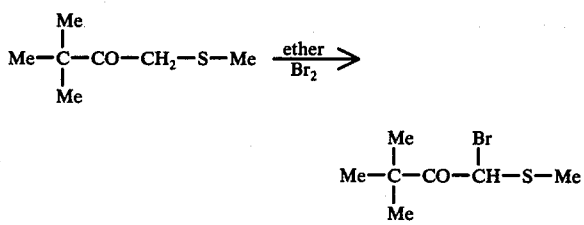

EXAMPLE 3

A solution of 7.41 g (0.05 mole) of N-butyrophenone and a trace of AlCl₃ in 15 ml anhydrous ethyl ether was brominated using 8.0 g (2.65 ml; 0.05 mole) of bromine. The ether and the bromine were removed by in vacuo. The resulting oil was diluted to 100 ml with absolute ethanol and mixed with 5.809 g (0.05 mole) of 3,4,5,6,-tetrahydro-2-pyrimidine thiol. This material was refluxed for 18 hours. The crude product which was obtained on cooling the reaction mixture was recrystallized from 95% ethanol. Recovery was 8.09 g (49.74%) of a white solid which was analyzed and found to be 2-ethyl-3-phenyl-4,5,6,7-tetrahydrothiazole[3,2-a] pyrimidine hydrobromide.

It should be noted that the intermediates, e.g., hydrated compounds, may be produced by well known variations of the foregoing general techniques. For example, they can be obtained by not refluxing but simply heating to a temperature of about 25° C.

EXAMPLE 4

The compounds of the present invention have pharmaceutical activity as antiinflammatory agents, effective in the prevention and inhibition of granuloma tissue formation. The activity is demonstrated by a test which involves the diminution of experimental edema induced in the hind paw of a rat by the injection of carrageenin.

The procedure used for measuring the inhibition of carrageenin-induced edema is a slight modification of the method of Winter et al., Proc. Soc. Explt. Biol. Med. 111:544 (1962). The device used for measurement of the paw volume is an adaptation of the water displacement procedure described by Adamkiewicz et al., Can. J. Biochem. Physiol. 33:332 (1955). The above compounds were studied for their effectiveness in preventing the edema caused by the intraplantar injection of 0.05 ml of a sterile 1.0% solution of carrageenin. Compounds were administered orally, except when indicated as intraperitoneally (i.p.), 1 hour prior to the injection of the carrageenin into the left hind paw of rats. At peak swelling time (3 hours) the volume of edema was calculated by differential paw volumes.

Table I (in which Ph = phenyl) sets forth results obtained at the indicated dosages with compounds (or their salts) of the formula:

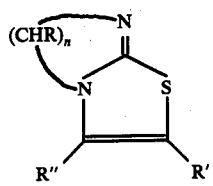

TABLE I

| Compound | n= | R= | R'= | R"= | Salt | Dose (mg/kg) | Reduction % |
|---|---|---|---|---|---|---|---|
| 1 | 2 | H,H | H | Ph | HBr | 50 | 47 |
| 2 | " | " | H | 3,4-diCH$_3$Ph | " | " | 27 |
| 3 | " | " | SCH$_3$ | C(CH$_3$)$_3$ | " | " | 26 |
| 4 | " | " | C$_2$H$_5$ | Ph | " | 25 | 41 |
| 5 | " | " | C$_2$H$_5$ | p-ClPh | " | " | 33 |
| 6 | " | " | CH$_3$ | " | " | " | 45 |
| 7 | " | " | H | p-BrPh | " | 50 | 70 |
| 8 | " | " | H | C(CH$_3$)$_3$ | H tartrate | " | 56 |
| 9 | " | " | H | CH$_3$ | HCl | " | 46 |
| 10 | " | " | H | α-naphthyl | HI | " | 58 |
| 11 | " | " | H | C(CH$_3$)$_3$ | none | " | 48 |
| 12 | " | CH$_3$,H | H | C(CH$_3$)$_3$ | HBr | " | 54 |
| 13 | " | CH$_3$,H | H | CH$_3$ | HCl | " | 24 |
| 14 | " | H,H | CH$_3$ | Ph | HBr | " | 49 |
| 15 | " | H,H | Ph | CH$_3$ | HBr | " | 53 |
| 16 | " | CH$_3$,H | H | p-ClPh | HBr | " | 58 |
| 17 | " | CH$_3$,H | H | p-NO$_2$Ph | HBr | " | 48 |
| 18 | " | CH$_3$,H | H | 3,4-diClPh | HBr | " | 42 |
| 19 | 2 | H,H | CH$_2$COOH | Ph | HBr | 100ip | 24 |
| 20 | " | " | H | Ph | 3,4-diCl-benzyl Cl | 20 | 36 |
| 21 | " | " | H | p-BrPh | none | 40 | 49 |
| 22 | " | " | H | " | propargyl Br | 100 | 36 |
| 23 | " | " | H | " | α-methyl propargyl Cl | 40 | 27 |
| 24 | " | " | H | " | 4-chloro-2-buteneyl Cl | 60 | 20 |
| 25 | " | " | H | CH$_3$ | none | 150 | 44 |
| 26 | " | " | H | CH$_3$ | propargyl Br | 40 | 31 |
| 27 | " | " | H | 2-benzofuranyl | HBr | 40 | 40 |
| 28 | 3 | 3H | H | p-ClPh | " | 25 | 29 |
| 29 | " | " | C$_2$H$_5$ | Ph | " | 50 | 76 |
| 30 | " | " | H | Ph | " | 40 | 25 |
| 31 | " | " | CH$_3$ | Ph | " | 40 | 48 |
| 32 | " | " | H | p-NO$_2$Ph | " | 25 | 20 |
| 33 | " | " | CH$_3$ | p-ClPh | " | 10 | 22 |

All compounds show a positive effect, which may be increased by the use of larger dosages.

EXAMPLE 5

Following the procedure set forth in Example 4, hydrated compounds according to the following formula were evaluated for antiinflammatory effect with the results shown in Table II:

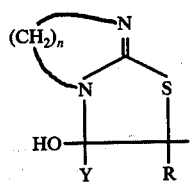

TABLE II

| Compound | n= | Y= | R= | Salt | Dose (mg/kg) | Reduction (%) |
|---|---|---|---|---|---|---|
| 34 | 2 | Ph | H | HBr | 100 | 70 |
| 35 | 2 | Ph | CH$_3$ | " | 150 | 68 |
| 36 | 2 | p-ClPh | H | " | 25 | 57 |
| 37 | 3 | Ph | H | " | 50 | 52 |
| 38 | 3 | p-ClPh | H | " | 100 | 76 |

TABLE II-continued

| Compound | n= | Y= | R= | Salt | Dose (mg/kg) | Reduction (%) |
|---|---|---|---|---|---|---|
| 39 | 3 | p-CH$_3$OPh | H | " | 40 | 27 |

EXAMPLE 6

Certain of the compounds of the invention were further tested to determine their ED$_{50}$ values. The ED$_{50}$ value is defined as that dose which reduced edema formation by about 25% or more compared with the mean control response (parallel run) in 50% of the animals. Typical results of these tests appear in Table III.

TABLE III

| | ED$_{50}$ vs. CARRAGEENIN ASSAY | | |
|---|---|---|---|
| Compound | Dose (mg/kg) | ED$_{50}$ (mg/kg) | Confidence Limits |
| 1 | 25, 75, 100, 150 | 25 | 18–32 |
| 9 | 25, 50, 75, 100 | 20 | 16–24 |

EXAMPLE 7

Next, certain of the compounds were subjected to a secondary screen designated the adrenalectomized assay. In this series of tests, the method used was identical to that described above, except that the animals used were adrenalectomized several days prior to assay. Since the results in the nonadrenalectomized animals were similar to those obtained in the adrenalectomized animals, it can be inferred that the antiinflammatory activity of the test compounds was not caused by the release of endogenous adrenocortical steroids.

The results of this test are given in Table IV.

TABLE IV

| Adrenalectomized Sprague Dawley Male Rats (Charles River) | | |
|---|---|---|
| Compound | % Reduction | Dose at mg/kg |
| 1 | 32 | 50 |
| 4 | 31 | 25 |
| 5 | 15 | 25 |
| 6 | 19 | 25 |
| 8 | 23 | 25 |
| 9 | 46 | 25 |
| 10 | 18 | 50 |
| 16 | 16 | 50 |
| 17 | 60 | 50 |
| 29 | 18 | 25 |

EXAMPLE 8

Selected compounds were further subjected to advanced evaluations. Specifically, in view of the interesting activity of compounds 1 and 9, those compounds were further subjected to the adjuvant-induced arthritis test. This test requires one month (from day 0 to day 31 ). In the first seventeen days (0–17), the disease is in a developing stage, while for the remainder of the month (18–31) the disease is fully developed. The results of this test, given in terms of percent reduction of swelling in the hind paw of the rat are shown in Table V.

The method is essentially that of Newbould, Brit. J. Pharmacol. 21:127, 1963. The test compounds were studied in the developing arthritis state and in the established arthritic state. Separate groups of twelve rats were administered the compounds orally using methylcellulose as the vehicle. In the study on the developing disease, administration of the test compounds begins on day 1 and on day 2 each animal is injected with 0.05 ml/kg of a 0.5% suspension of heat-killed *Mycobacterium tuberculosis* into the planter surface of the left hind paw. Foot volumes were measured by a water displacement device on the day of administration of the Mycobacterium and again on days 3, 10 and 17. The test compounds were administered once daily. Body weights were recorded daily and the animals were examined for the spread of the inflammation and the degree of secondary lesions. For study in the established disease, another group of rats are injected with the Mycobacterium and foot volumes are measured. After twenty days volumes are again measured and administration of the test compounds begins and continues for eleven days. Foot volume measurements are repeated on day 27 and day 31. The extent of the spread of the inflammation and the degree of lesions are recorded daily as are the body weights. The effect of the test compounds is measured by the percentage reduction in left hind paw volumes as compared to the hind paw volumes of the control groups.

TABLE V

| ADJUVANT ARTHRITIS TEST IN RATS % REDUCTION IN SWELLING-HIND PAWS | | | | | | |
|---|---|---|---|---|---|---|
| | | Days | | | | |
| | | Developing (propylactic) | | | Developed (therapeutic) | |
| Compound | Dose (mg/kg) | 3 | 10 | 17 | 20 | 27 | 31 |
| 1 | 20 | 18 | 13 | 18 | 5 | 0 | 0 |
|   | 40 | 10 | 21 | 43 | 4 | 14 | 8 |
| 9 | 24 | 21 | 23 | 15 | 5 | 0 | 0 |
|   | 50 | 18 | 17 | 6 | 3 | 3 | 7 |

In addition to the reduction in inflammation indicated in Table V, a lessening in the degree of secondary lesions was observed.

We claim:

1. A method of treating inflammation in an animal subject comprising administering to said subject a nontoxic antiinflammatory amount of a compound of the formula:

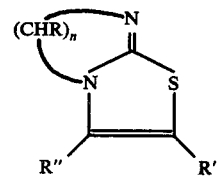

wherein $n$ is 3; R is hydrogen or methyl; R' is hydrogen, $C_1$–$C_3$ alkyl or thioalkyl, phenyl, or carboxy methyl; and R" is $C_1$–$C_4$ alkyl, 2-benzofuranyl, naphthyl, phenyl, or mono- or disubstituted phenyl, or an acid addition or quaternary salt thereof.

2. The method as defined in claim 1 wherein said nontoxic antiinflammatory amount ranges between about 10 to about 500 mg/kg/day.

3. The method as defined in claim 1 wherein said compound is 2-methyl-3-phenyl-4,5,6,7-tetrahydrothiazolo [3,2-a]-pyrimidine.

4. The method as defined in claim 1 wherein said compound is 3-phenyl-4,5,6,7-tetrahydrothiazo[3,2-a] pyrimidine.

5. A method of treating inflammation in an animal subject comprising administering to said subject a nontoxic antiinflammatory amount of a compound of the formula:

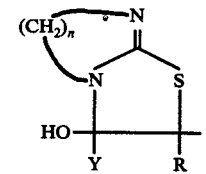

wherein $n$ is 3; R is hydrogen or methyl; and Y is phenyl or p-chloro- or p-methoxyphenyl, or an acid addition or quaternary salt thereof.

6. The method as defined in claim 5, wherein said nontoxic antiinflammatory amount ranges between about 10 to about 500 mg/kg/day.

7. The method as defined in claim 5 wherein said compound is 3-phenyl-3-hydroxy-2,3,6,7-tetrahydrothiazolo[3,2-a]-pyrimidine.

* * * * *